United States Patent [19]

McMahon

[11] Patent Number: 4,883,915

[45] Date of Patent: Nov. 28, 1989

[54] CATALYZED OXIME CONVERSIONS

[75] Inventor: Patrick E. McMahon, Wheaton, Ill.

[73] Assignee: Amoco Corporation, Chicago, Ill.

[21] Appl. No.: 35,868

[22] Filed: Apr. 8, 1987

Related U.S. Application Data

[62] Division of Ser. No. 870,822, Jun. 5, 1986, Pat. No. 4,697,010.

[51] Int. Cl.$^4$ .................. C07D 103/38; C07D 201/04; C07D 103/365
[52] U.S. Cl. .................................. 564/155; 564/158; 564/214; 564/152; 564/156; 540/535; 540/536
[58] Field of Search ........................ 564/155, 158, 214

[56] References Cited

U.S. PATENT DOCUMENTS

| | | | |
|---|---|---|---|
| 3,503,958 | 3/1920 | Landis | 540/535 |
| 4,359,421 | 11/1982 | Bell et al. | 540/535 |
| 4,697,010 | 9/1987 | McMahon | 540/536 |

OTHER PUBLICATIONS

Pauling "General Chemistry" 1st Ed., (Freeman)(1947) pp. 343–345.
Pawling "General Chemistry"3rd Ed., (Freeman)(1970) pp. 568–569.
Jerry March "Advanced Organic Chemistry": Reations Mechanisms and Structure (McGraw-Hill)(1968) pp. 226–227, 821–822.
Scott et al., Journal of Organic Chemistry, vol. 19, pp. 1815–1823 (1954).
Carey and Sundberg "Advanced Organic Chemistry" 2nd Edition, pp. 449–450 and 470 (Plenum)(1983).

*Primary Examiner*—Robert T. Bond
*Attorney, Agent, or Firm*—Reed F. Riley; William H. Magidson; Ralph C. Medhurst

[57] ABSTRACT

A process for the catalyzed conversion fo oximes such as cyclohexanone oxime to amides such as caprolactam via a high conversion, high selectivity, long catalyst lifetime reaction over a HAMS-1B crystalline borosilicate-based catalyst composition.

6 Claims, No Drawings

CATALYZED OXIME CONVERSIONS

This is a division of application Ser. No. 870,822, filed June 5, 1986, now U.S. Pat. No. 4,697,010.

BACKGROUND OF THE INVENTION

This invention relates to an improved process for the catalyzed conversion of oximes to amides which employs a HAMS-1B crystalline borosilicate-based catalyst composition. More particularly, this invention relates to the high conversion, high selectivity, and long catalyst life-time, gas phase catalyzed conversion of cyclohexanone oxime to caprolactam over a HAMS-1B crystalline borosilicate-based catalyst composition.

Caprolactam is a large volume commodity chemical used as a monomer in the production of the commercially important Nylon-6. Although routes to the precursor cyclohexanone oxime vary, all commercial caprolactam production makes use of a Beckmann rearrangement of the oxime. The commercial reaction is carried out in a batch operation in oleum ($H_2SO_4 \cdot SO_3$) solution. The recovery step in this technology employs an ammonium hydroxide neutralization of the resulting caprolactam-oleum solution, a process generating two mols of by-product ammonium sulfate per mol of product. The sulfate has some value as a low grade fertilizer, but its disposal can add substantial cost to Nylon-6 production. Attempts have been made to circumvent the use of oleum and carry out the reaction in the gas phase; for example, BASF in a series of patents describes a supported catalyst containing boric acid (boric oxide) for the gas phase molecular rearrangement of cyclohexanone oxime to caprolactam in a fluidized bed. See e.g., Ger. Offen. Nos. 1,670,816, 2,059,703, and 2,641,429. Mobil, in Eur. Pat. Appl. No. 0056 698, teaches a gas phase process for the manufacture of the lactam by passing cyclohexanone oxime over a ZSM aluminosilicate molecular sieve catalyst having a $SiO_2$ to $Al_2O_3$ ratio of at least 12 and a Constraint Index of 1 to 12. Others have carried out the same reaction in the gas phase over polyphosphoric acid, U.S. Pat. No. 3,016,375, and over Zeolite Y. See J. Cat. 6, 247–53 (1966). Russian workers have used catalysts made from zeolites modified with amorphous aluminum borate or a mixture of aluminum oxide and boric oxide. See Dokl, Akad. Nauk., SSSR 26, 47 (1982) and Russian Inventor's Certif. Nos. 755,295 and 891,146. The last publication claims that the zeolite prepared by "simultaneous precipitation of aluminum and silicon hydroxide from aqueous solutions of their salts with subsequent modification with boric acid and addition of 30% decationized zeolite Y-type suspension" is a borosilicate. However, it is highly unlikely that the Russian material contains boron in the lattice and it is believed that none of the catalysts described combine high selectivity and catalyst lifetime with high conversion, a combination of prime importance for a commercial catalyst.

Now, it has been found that a catalyst composition comprising a supported HAMS-1B crystalline borosilicate sieve is capable of 100% conversion of cyclohexanone oxime to caprolactam at a selectivity to the caprolactam of over 80%. Additionally, the high conversion and selectivity can remain essentially constant over a very long catalyst composition lifetime.

SUMMARY OF THE INVENTION

Described herein is a process comprising contacting in the gas phase under reaction conditions cyclohexanone oxime together with an inert diluent with a catalyst composition comprising a HAMS-1B crystalline borosilicate molecular sieve incorporated into an inorganic matrix to form caprolactam.

DETAILED DESCRIPTION OF THE INVENTION

The process of the instant invention preferably employs an oxime or dioxime of cyclohexanone, 4,4'-diacetylphenylether, or 2,6-diacetylnaphthalene. More preferably, cyclohexanone oxime is the feed to the process. The feed is preferably diluted prior to or after introduction into the reactor with an essentially inert material, preferably a hydrocarbon. The material should be essentially inert to the feed and to the product and additionally should be essentially inert to the catalyst composition itself. The inert material desirably dissolves the oxime or dioxime so the latter can be introduced more conveniently into the reactor. Preferred materials are lower boiling saturated hydrocarbons such as hexane and aromatic compounds such benzene.

The reaction is desirably carried out in a fixed bed reactor although an ebullated or fluidized bed or other type of reactor can be useful, too, with appropriate changes in the reactor conditions and physical makeup of the catalyst, as may be understood by one skilled in the art.

The reaction is desirably carried out in the temperature range between about 150° and about 500° C., more preferably between about 200° and about 400° C. Although the reaction can be carried out at atmospheric pressure, elevated pressure from about 10 psig to about 400 psig, more preferably from about 50 psig to about 300 psig, is desirable. In a fixed bed reactor, the WHSV (weight hourly space velocity) desirably varies from about 2 to about 100, more preferably from about 5 to 50.

In feeding the oxime to the reactor is it desirable to dilute it by adding a diluent chosen from inorganic or organic materials which do not interfere with the desired reaction. The mol ratio of diluent to oxime is preferably between about 50/1 and about 1/1, more preferably between about 30/1 and about 5/1.

The catalyst compositions used in this invention are based on AMS-1B crystalline borosilicate molecular sieve, which is described in U.S. Pat. Nos. 4,268,420, 4,269,813, and 4,285,919 and Published European Patent Application No. 68,796, all incorporated herein by reference. AMS-1B crystalline borosilicate generally can be characterized by the X-ray pattern listed in Table A and by the composition formula:

$$0.9 \pm 0.2 M_{2/n}O:B_2O_3:ySiO_2:zH_2O$$

wherein M is at least one cation, n is the valence of the cation, y is between 4 and about 600 and z is between 0 and about 160.

TABLE A

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |

TABLE A-continued

| d-Spacing Å (1) | Assigned Strength (2) |
|---|---|
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having a valence n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical although a typical procedure is to dissolve base and boric acid in water and then add the template compound. Generally, the silicon oxide compound is added with intensive mixing such as that performed in a Waring Blender and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be about above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1 and most preferaly about 0.2 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass, and a subsequent activation or calcination procedure is necessary, if it is desired to remove this material from the final product. Typically, mildly dried product is calcined at temperatures ranging from about 260° to about 850° C. and preferably about 425°; to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form. If the sieve was prepared using a metal hydroxide, such as sodium hydroxide, the hydrogen form typically is produced by exchanging one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Examples of catalytically active elements include ruthenium, rhodium, iron, cobalt, and nickel. Mixtures of elements can be used. Other catalytic materials include ions and compounds of aluminum, lanthanum, molybdenum, tungsten, and noble metals such as ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, cobalt, iron, zinc and cadmium. Specific combinations of non-noble metals of Group VIII and other catalytic materials include ions or compounds of nickel and osmium, nickel and lanthanum, nickel and palladium, nickel and iridium, nickel and molybdenum, and nickel and tungsten.

Ion exchange and impregnation techniques are well known in the art. Typically, an aqueous solution of a cationic species is exchanged one or more times at about 25° to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about thirty weight percent, typically from about 0.05 to about 25 weight percent, depending on the process use intended. The optimum amount can be determined easily by routine experimentation.

The AMS-1B crystalline borosilicate useful in this invention is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending wit a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt.% of the total composition. Catalytic compositions can contain about 0.1 wt.% to about 100 wt.% crystalline borosilicate material and preferably contain about 10 wt.% to about 95 wt.% of such material and most preferably contain about 20 wt.% to about 80 wt.% of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

The following Examples will serve to illustrate certain embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

Example I

All oxime conversions were carried out in a ¾ inch o.d. glass tube containing 4 cc of catalyst fitted with a fretted catalyst zone and a glass thermowell. Heating of the reactor tube was accomplished using a single zone tube furnace. The feed to the reactor was a liquid, which was pumped and measured by a syringe pump. Gas flows were measured using a bubble flowmeter.

The oxime was dissolved in benzene as a 5 wt.% solution and pumped into the reactor where it was vaporized using nitrogen gas introduced at a flow rate of 40 cc per minute. The LHSV was held at about 1.0 and the temperature and pressure of the reactor was held at about 300° C. and about 1 atmosphere, respectively. Product was condensed in a cooled vessel after exiting the reactor and was analyzed by gas chromatography. Identification of the components of the product was accomplished through the use of gas chromatograph-mass spectrographic analysis. Conversion and selectivity data in weight percent for samples taken after the catalyst composition was 20 hours on stream are shown in Table I below. All catalyst compositions are in weight percent.

TABLE I

Conversions and Selectivities for the Catalyzed Conversion of Cyclohexanone Oxime to Caprolactam

| Catalyst Composition | Example No. | Conversion (Wt %) | Selectivity (Wt % lactam) | Selectivity (Wt % ketone) | Selectivity (Wt % aniline) |
|---|---|---|---|---|---|
| HAMS-1B[1] | | 100 | 82 | 10 | 2.5 |
| HAMS-1B[2] | | 100 | 78 | 11 | 2.5 |
| HAMS-1B[3] (20% Mg) | | 98 | 78 | 9 | 3.5 |
| HAMS-1B[4] (3% Mo) | | 95 | 60 | 30 | |
| $\gamma$-Al$_2$O$_3$[5] | | 100 | 30 | 33 | |
| H$_3$PO$_4$ on SiO$_2$ | 2 | 100 | 54 | 15 | 2.0 |
| ZSM-5 | 3 | 98 | 40 | 14 | |
| Silicalite | 4 | 100 | 74 | 10 | 2.0 |
| Al$_2$O$_3$.B$_2$O$_3$ | 5 | 29 | 82 | 6 | |

[1]Sieve made according to European Patent No. 68796, Example 8. Composition is 40% sieve and 60% $\gamma$-Al$_2$O$_3$.
[2]Made according to U.S. Pat. No. 4,268,420, Example 6. Composition is 35% sieve and 60% $\gamma$-Al$_2$O$_3$.
[3]See footnote 1. Impregnated by treating the catalyst composition with magnesium nitrate, drying and calcining. Final composition contains 20% by weight magnesium, probably as the oxide.
[4]Made according to the procedures taught in U.S. Pat. No. 4,268,420. The sieve was impregnated with Mo by treating with ammonium molybdate, drying, and calcining. Composition is 20% sieve and 80% $\gamma$-Al$_2$O$_3$.
[5]Made by gelling PHF Al$_2$O$_3$ sol (American Cyanamid) with NH$_4$OH, drying at 165° C. and calcining at 540° C., Example 2

A 12.23 g portion of 85% aqueous phosphoric acid was diluted with sufficient water to give 25 ml of solution. A 5.8 ml portion of the solution was added to a beaker containing 7.5 g of silica. The mixture was stirred until the solid was uniformly moist and dried in an oven overnight at 125° C. The material contains about 8% by weight phosphorus, about 45% by weight silicon and has a surface area of about 70 sq m/g.

Example 3

A 37.2 g portion of NaOH was dissolved in 400 ml of distilled water and then, sequentially, a 207.9 g portion of tetrapropylammonium bromide and a 42 g portion of sodium aluminate were added and dissolved. After adding with mixing a 1077 g portion of HS-40 Ludox colloidal silica, the mass was diluted to 1800 ml total volume with distilled water. After brief stirring the mass was transferred to a telfon-lined autoclave and heated under autogeneous pressure for 6 days. After cooling and filtering, the solid was washed 3 times, dried overnight at 121° C., and calcined at 538° C. for 4 hours. A 441 g portion of the calcined solid was exchanged by slurrying 3 times with an equal weight of ammonium nitrate dissolved in 3 liters of distilled waer. The result was washed 3 times with distilled water, heated overnight at 121° C., and calcined at 538° C. for 4 hours. The resulting sieve was 74% crystalline as ZSM-5 by XRD and contained 32 ppm of Na and 2.24% Al.

To make an alumina-supported material, 40 g of the sieve was mixed in a Waring Blendor with 500 g of a 12% solids alumina sol and enough concentrated ammonia added to gel the mixture. The gel was dried overnight at 121° C. and then calcined at 538° C. for 4 hours. The resulting catalyst composition was 40% sieve and 60% $\gamma$-alumina.

Example 4

A solution employing 886 g of distilled water, 95.73 g of ethylenediamine and 62.03 g of tetrapropyl ammonium bromide was made which had a pH of 11.85. A 396.51 g portion of Du Pont Ludox AS-40 was added to the solution and stirred for 15 minutes. This mixture was digested 4 days at 150° C. under autogeneous pressure. The mixture was filtered and the solid sieve dried 4 hours at 165° C. and calcined for 12 hours at 540° C. The resulting silicalite was 93% crystalline as determined by XRD.

Example 5

A 42.7 g portion of boric acid was dissolved with heating in a mixture of 200 ml of water and 110 ml of concentrated ammonium hydroxide. The resulting warm solution was added to 399 g of Du Pont PHF alumina sol with stirring and the resulting gel transferred to a crystallizing dish. This procedure was repeated and the resulting gels combined and dried in an air-purged oven at 150° C. for 64 hours. The resulting solid was calcined 4.5 hrs. at 540° C., crushed, and all the material not passing through a 40 mesh sieve (115.3 g) was retained. The sieved material was analyzed giving 9.6% by weight boron and 33.9% by weight Al. The solid is amorphous by XRD, has a surface area by BET of 158 m$^2$/g. It exhibits a pore volume of 0.908 cc/g and an average pore radius of 129 Å using the Digasorb technique.

Example 6

The conversion of 2,2,4-trimethylcyclohexanone oxime to its lactam using HAMS-1B catalyst composition (40% by weight on $\gamma$-Al$_2$O$_3$) was made under process conditions identical to those set forth in Example 1. Conversion and selectivity to tha lactam were 95-98% and 82-85%, respectively, after the catalyst composition had been onstream 20 hours.

Example 7

A lifetime study of a HAMS-1B (40% by weight on $\gamma$-Al$_2$O$_3$) catalyst composition was made using the process conditions of Example 1. The data is shown in Table II below.

TABLE II

HAMS-1B (40% on $\Gamma$Al$_2$O$_3$) Catalyzed Oxime Conversion Lifetime Study

| Time on Stream (hrs) | Conversion (Wt %) | Selectivity (Wt %) |
|---|---|---|
| 54 | 100 | 81 |
| 100 | 100 | 81 |
| 175 | 100 | 81 |
| 191 | 100 | 81 |
| 215 | 100 | 81 |

TABLE II-continued

HAMS-1B (40% on ΓAl$_2$O$_3$) Catalyzed Oxime Conversion
Lifetime Study

| Time on Stream (hrs) | Conversion (Wt %) | Selectivity (Wt %) |
|---|---|---|
| 223 | 96 | 84 |

What is claimed is:

1. A process comprising contacting under reaction conditions the oxime or dioxime of 4,4'-diacetylphenylether together with an inert diluent and a catalyst composition comprising a HAMS-1B crystalline borosilicate molecular sieve incorporated into an inorganic matrix to form N,N'-diacetyloxy(bis)aniline.

2. The process of claim 1 wherein said sieve comprises from about 20 to about 80 wt.% incorporated into an alumina, silica or silica-alumina matrix.

3. The process of claim 1 wherein said sieve comprises from about 20 to about 80 wt.% incorporated into an alumina matrix.

4. A process comprising contacting under reaction conditions the oxime or dioxime of 2,6-diacetylnaphthalene together with an inert diluent and a catalyst composition comprising a HAMS-1B crystalline borosilicate molecular sieve incorporated into an inorganic matrix to form N,N'-diacetyl-2,6-diaminonaphthalene.

5. The process of claim 4 wherein said sieve comprises from about 20 to about 80 wt.% incorporated into an alumina, silica or silica-alumina matrix.

6. The process of claim 4 wherein said HAMS-1B molecular sieve comprises from about 20 to about 80 wt.% incorporated into an alumina matrix.

* * * * *